United States Patent [19]

Hoenes

[11] Patent Number: 5,334,508
[45] Date of Patent: Aug. 2, 1994

[54] PROCESS AND AGENT FOR THE COLORIMETRIC DETERMINATION OF AN ANALYTE BY MEANS OF ENZYMATIC OXIDATION

[75] Inventor: Joachim Hoenes, Weinheim, Fed. Rep. of Germany

[73] Assignee: Boehringer Mannheim GmbH, Fed. Rep. of Germany

[21] Appl. No.: 4,587

[22] Filed: Jan. 14, 1993

Related U.S. Application Data

[62] Division of Ser. No. 390,946, Aug. 9, 1989, Pat. No. 5,206,147.

[30] Foreign Application Priority Data

Aug. 9, 1988 [DE] Fed. Rep. of Germany ....... 3826922

[51] Int. Cl.$^5$ .................... C12Q 1/26; C12N 9/02; C12N 9/04; C12N 9/06; C12N 9/08
[52] U.S. Cl. .................... 435/25; 435/189; 435/190; 435/191; 435/192
[58] Field of Search .............. 435/189, 190, 191, 192, 435/25

[56] References Cited

U.S. PATENT DOCUMENTS

| | | | |
|---|---|---|---|
| 4,105,800 | 8/1978 | Jahns et al. | 435/188 |
| 4,576,913 | 3/1986 | Adachi et al. | 435/26 |
| 4,629,689 | 12/1986 | Diamond et al. | 435/6 |
| 4,645,760 | 2/1987 | Pierson | 514/36 |

FOREIGN PATENT DOCUMENTS

| | | |
|---|---|---|
| 0120440 | 10/1984 | European Pat. Off. |
| 0296481 | 12/1988 | European Pat. Off. |
| 3820404 | 12/1988 | Fed. Rep. of Germany |
| 2239999 | 10/1987 | Japan |

OTHER PUBLICATIONS

Database WPIL/Derwent, Abstract No. 87-062511 (09), 1987, Derwent Publications Ltd., London, GB; and JP-A-62019099 (Sapporo Breweries) 27.01.1987.

Jongejan et al., Kluwers Academic Press (1988) pp. 100-102.
Walsh (1980) Acc. Chem. Res., 13, 148-155.
Walsh (1979) "Enzmatic Reaction Mechanisms", pp. 432-433, Freeman, San Francisco.
Merck Index (1983) p. 1174, #8037, Merck & Co., Rahway, N.J.
Oyanagui (1984) Anal. Biochem, 142, 290-296.
Biaglow et al. (1977) Cancer Res. 37(9), 3306-3313 from Biological Abstracts (1978) 275, Ab #2915.
Ramer et al., (1988) J. Am. Chem. Soc. 110(25), 8526-8532.
Edmondson et al., (1985) Proc. Natl. Acad. Sci., USA, 82, 682-683.
Benkovic (1980) Ann. Rev. Biochem., 49, 227-251.
McIntire et al. (1991) Science, 252, 817-824.
Skursky et al. (1979) *Anal. Biochem.*, 99, 65-71.
Kovar et al. (1986) *Biochem. J.*, 235, 537-543.

*Primary Examiner*—Douglas W. Robinson
*Assistant Examiner*—Jon P. Weber
*Attorney, Agent, or Firm*—Nikaido, Marmelstein, Murray & Oram

[57] ABSTRACT

The present invention provides a process for the colorimetric determination of an analyte by means of enzymatic oxidation of the analyte in the presence of an electron acceptor and determination of the reduced electron acceptor by color formation as measure for the amount of the analyte, wherein the analyte is oxidized with an appropriate oxidoreductase in the presence of a substance selected from the group of compounds with nitrogen in an oxidation stage between +1 and −1 as direct electron acceptor.

The present invention also provides an agent for the colorimetric determination of an analyte by enzymatic oxidation of the analyte, containing an oxidoreductase and a color-forming electron acceptor, wherein the color-forming electron acceptor is a substance reacting directly with the analyte/enzyme system selected from the group of compounds with nitrogen in an oxidation stage between +1 and −1.

20 Claims, 3 Drawing Sheets

PROCESS AND AGENT FOR THE COLORIMETRIC DETERMINATION OF AN ANALYTE BY MEANS OF ENZYMATIC OXIDATION

This is a division of application Ser. No. 07/390,946 filed Aug. 9, 1989, now U.S. Pat. No. 5,206,147.

The present invention is concerned with a process for the colorimetric determination of an analyte by means of enzymatic oxidation of the analyte in the presence of an electron acceptor and determination of the reduced electron acceptor by colour formation as a measure for the amount of the analyte.

Furthermore, the present invention is concerned with an agent for the colorimetric determination of an analyte by enzymatic oxidation of the analyte containing an oxidoreductase and a colour-forming electron acceptor.

The present invention especially extends to the use of a substance selected from the group comprising compounds with nitrogen in an oxidation stage between +1 and −1 as a direct electron acceptor of an analyte/oxidase system or of an analyte/NAD(P)-independent dehydrogenase system.

The present invention is especially concerned with the use of a substance selected from the group comprising nitroso compounds, hydroxylamines and oximes as a colour-forming electron acceptor in the case of the oxidation of an analyte by means of an oxidoreductase.

In analyses, enzymatic oxidations make possible the detection and determination of substances in the most varied sample materials. An oxidising enzyme thereby acts on a corresponding enzyme substrate in the presence of an acceptor accepting the electrons of the oxidation reaction. The reduction of the electron acceptor shows the presence of the enzyme substrate. Hitherto, it has thereby proved to be especially advantageous when the reduced electron acceptor can be detected by a colour formation since this is possible not necessarily only by means of expensive measurement apparatus but can possibly also take place visually.

Known methods for the colorimetric determination of substances by means of oxidising-acting enzymes use oxidases or dehydrogenases. Both groups of enzymes belong to the main group of the oxidoreductases (Römpps Chemie-Lexikon, Franckhsche Verlagshandlung, Stuttgart, 8th edition, 1985, Volume 4, page 2952; Lexikon Biochemie, pub. H. D. Jakubke, Verlag Chemie, Weinheim, 2nd edition, 1981, page 194), the members of which can be differentiated according to their natural electron acceptors.

The natural electron acceptor for oxidases is molecular oxygen (Römpps Chemie-Lexikon, Franckhsche Verlagshandlung, Stuttgart, 8th edition, 1985, Volume 4, page 2946). As representative for the state of the art of the use of oxidases for the colorimetric determination of analytes, there is mentioned A. Kunst et al. in "Methods in enzymatic analysis", pub. H. U. Bergmeyer, Verlag Chemie, Weinheim, 3rd edition, 1984, Volume 6, page 178–185. Glucose is there detected in serum, plasma or deproteinised blood by reaction with glucose oxidase and atmospheric oxygen in aqueous solution in that the hydrogen peroxide formed in the case of the reaction by reduction of the oxygen has an oxidising action and thus forms a colour with phenol and 4-aminophenazone also present in the reaction mixture. As a source of error, this literature reference mentions the presence of reducing-acting substances, such as ascorbic acid, uric acid or glutathione. Transition metal ions or haem and haem proteins, which can easily occur in samples derived from blood, also have a disturbing action because they decompose hydrogen peroxide. Sample component materials which lead to a colour formation with hydrogen peroxide and peroxidase and possibly further substances contained in the detection reagent, for example phenol or 4-aminophenazone, can give rise to false results. Such materials can be, for example, bilirubin or also medicaments, such as α-methyldopa, which can well be present in samples derived from blood or in urine.

J. Siedel et al. in "Methods in enzymatic analysis", pub.. H. U. Bergmeyer, Verlag Chemie, Weinheim, 3rd edition, 1984, Volume 8, page 139–148, describes the colorimetric determination of total cholesterol in serum or plasma in which ester-bound cholesterol is first liberated with cholesterol esterase. Cholesterol is then determined by reaction with cholesterol oxidase and atmospheric oxygen in aqueous solution, the hydrogen peroxide formed in the case of this reaction thereby oxidising in the presence of peroxidase and forming a coloration with phenol and 4-aminoantipyrine also present in the reaction mixture. The colour formation is a measure for the amount of total cholesterol in the sample.

All the disadvantages described for the above-mentioned processes for the determination of glucose by means of oxidase apply to the same extent to the described cholesterol determination method. These disadvantages are independent of whether the detection reaction is carried out, for example, in a cuvette or on a dry reagent carrier such as is known, for example, from European Patent Specifications Nos. 0,016,387, 0,262,445 and 0,256,806 and from Federal Republic of Germany Patent Specification No. 32 47 608. Especially in the case of carrying out the above-mentioned determination methods on solid carriers, i.e. in so-called dry tests, the oxygen requirement has additionally proved to be disadvantageous. In particular, when much oxygen is needed for the oxidation of high concentrations of enzyme substrate, the diffusion of oxygen from the air into the reaction medium can become the velocity-determining step and lead to long reaction times or, especially in the case of kinetic methods of determination, to false results.

Dehydrogenases can, quite generally, be subdivided into those which, for the oxidation of enzyme substrates, need nicotinamide-adenine-dinucleotide (NAD) or nicotinamide-adenine-dinucleotide phosphate (NADP) as natural direct electron acceptor and into those which are not NAD- or NADP-dependent and which thus use other substances as natural direct electron acceptors in the case of enzymatic oxidation reactions.

The use of dehydrogenases for colorimetric measurements is known, for example, from Federal Republic of Germany Patent Specification No.21 47 466. It is there described that lactate, by catalysis of lactate dehydrogenase, is reacted with nicotinamide-adenine-dinucleotide (NAD) to give pyruvate and reduced nicotinamide-adenine-dinucleotide (NADH). The NADH formed then reacts, for example in the presence of the enzyme diaphorase, with tetrazolium salts with the formation of NAD and coloured formazans, the concentration of which can be determined photometrically. Instead of diaphorase, there is also mentioned N-methylphenazinium methosulphate as a reduction catalyst for the transfer of electrons from NADH to the tetrazolium salt.

Disadvantages of this process are to be seen in the fact that, instead of NADH, other reducingly-acting substances possibly present in biological samples, for example blood, serum, plasma or urine, such as glutathione or medicaments, such as methyldopa or dobesilate, in the presence of reduction catalysts, such as diaphorase or N-methylphenazinium methosulphate, convert tetrazolium salts into corresponding formazans and thus give rise to falsely positive results.

Furthermore, the necessity of reduction catalysts, such as diaphorase or phenazinium sulphate, for the transfer of the electrons liberated by the oxidation of an analyte from analyte/enzyme system to an electron acceptor serving for the colour formation involve the disadvantage that other sample accompanying materials can also be reduced which under otherwise identical conditions, do not enter into a reduction but thus give rise to falsely negative results.

It is an object of the present invention to overcome the above-mentioned disadvantages of the prior art. In particular, it is an object of the present invention to provide a process for the analysis of especially biological fluids for the colorimetric determination of an analyte by means of enzymatic oxidation of the analyte in the presence of an electron acceptor and determination of the electron acceptor by colour formation as a measure of the amount of the analyte in which reducing-acting, especially hydrogen peroxide-decomposing accompanying materials in samples, especially biological samples, such as liquids derived from blood, for example serum, or in urine, do not disturb, which process avoids the use of reduction catalysts, such as diaphorase or N-methylphenazinium methosulphate, for which no oxygen is necessary and which thereby makes possible rapid colour end values even in the case of high substrate concentrations.

Furthermore, it is an object of the present invention to provide an agent for the colorimetric determination of an analyte by enzymatic oxidation of the analyte, which agent contains an oxidoreductase and a colour-forming electron acceptor which can be used for carrying out the above-mentioned process.

In particular, it is an object of the present invention to extend the choice of those substances which, as colour-forming electron acceptors, can be used for the improved process and agent as stated above.

Thus, according to the present invention, there is provided a process for the colorimetric determination of an analyte by means of enzymatic oxidation of the analyte in the presence of an electron acceptor and determination of the reduced electron acceptor by colour formation as measure for the amount of the analyte, wherein the analyte is oxidised with an appropriate oxidoreductase in the presence of a substance selected from the group of compounds with nitrogen in an oxidation stage between $+1$ and $-1$ as direct electron acceptor.

Furthermore, the present invention also provides an agent for the colorimetric determination of an analyte by enzymatic oxidation of the analyte, containing an oxidoreductase and a colour-forming electron acceptor, wherein the colour-forming electron acceptor is a substance reacting directly with the analyte/enzyme system selected from the group of compounds with nitrogen in an oxidation stage between $+1$ and $-1$.

In particular, we have found that the use of a substance selected from the group of compounds with nitrogen in an oxidation stage between $+1$ and $-1$ is especially suitable as direct electron acceptor of an analyte/oxidase system or of an analyte/NAD(P)-independent dehydrogenase system.

BRIEF DESCRIPTION OF THE DRAWING FIGURES

Figure 1:
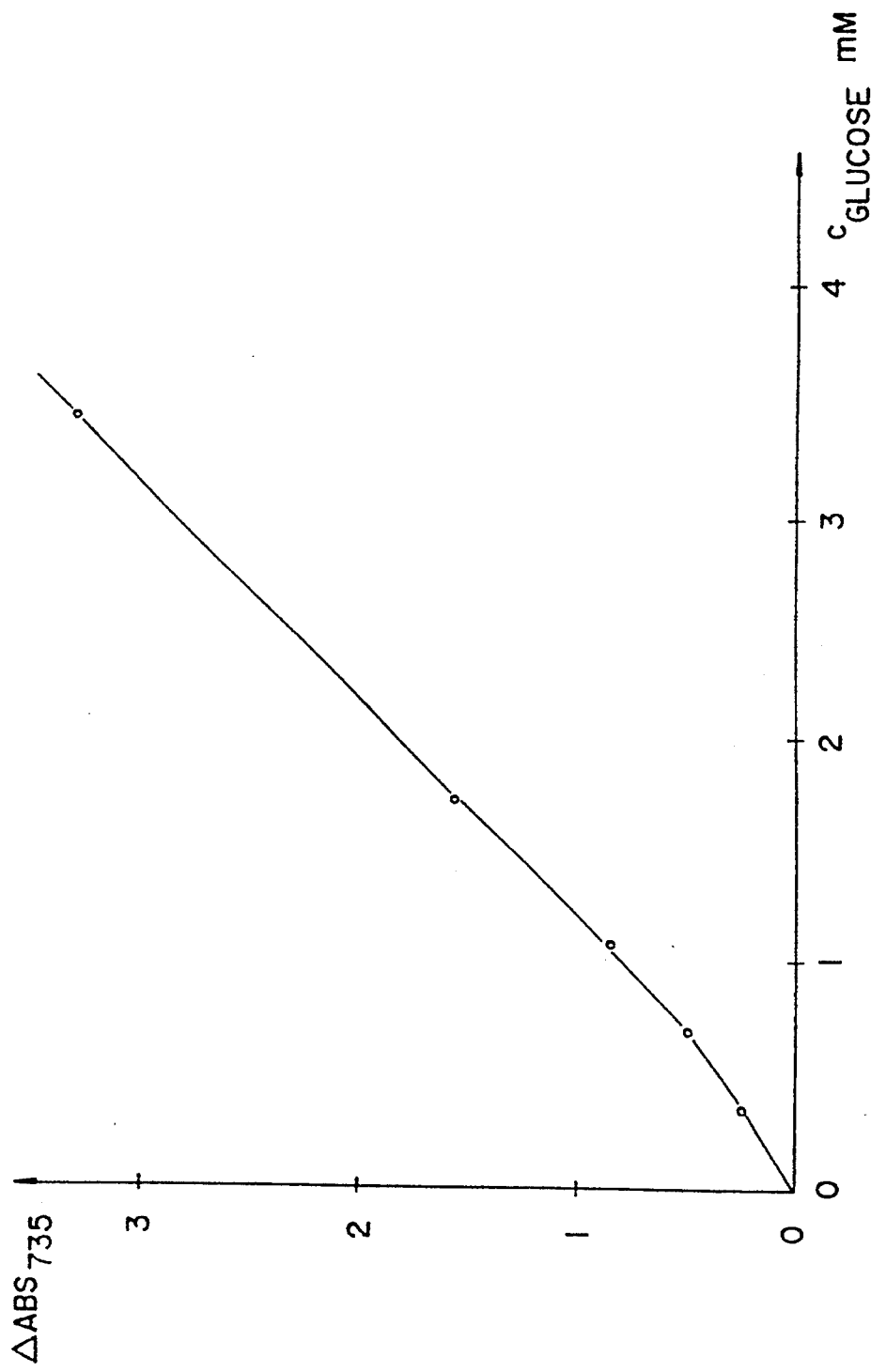
FIG. 1 is a plot of change of light absorption at 735 nm versus glucose concentration for a test sample described in Example 2.

According to the present invention, an "analyte" is to be understood to be a substance which is enzymatically oxidised. In many cases, the analyte will be the substance which is to be directly detected or quantitatively determined in the sample to be investigated. For example, glucose can be oxidised directly with glucose oxidase and determined colorimetrically. However, it is also possible that the analyte is first formed from another substance by one or more preceding reactions and thus, from the presence and concentration of the analyte, conclusions can be made indirectly regarding the presence and concentration of the starting substance. Thus, for example, glycerol can be so detected and determined by first converting glycerol by means of glycerol kinase and adenosine triphosphate into glycerol-3-phosphate and adenosine diphosphate and then subsequently, in a second reaction, oxidising the glycerol-3-phosphate with glycerol-3-phosphate oxidase. In this case, glycerol-3-phosphate is the analyte, the concentration of which corresponds to that of the substance to be determined, namely glycerol. However, here, too, the analyte is the compound which is determined colorimetrically.

In the present invention, the analyte is the substance which is accepted as substrate of the particular oxidising enzyme. In order that the analyte is oxidised, an electron acceptor must be simultaneously present which takes over the electrons from the analyte with the participation of the enzyme.

Surprisingly, we have now found that substances selected from the group of compounds with nitrogen in an oxidation stage between $+1$ and $-1$ and preferably those with nitrogen in an oxidation stage of $+1$ or $-1$ can be used as colour-forming electron acceptors for oxidising enzymes.

By "colour-forming" is to be understood in this connection that the electron acceptor after reduction is either itself directly present with a colour different from that before the enzymatic oxidation of the analyze or that the reduced acceptor itself admittedly does not lead directly to a colour production but, in a following reaction, causally leads to a colour change of the reaction mixture. Colour change hereby includes not only the change from colourless to coloured but also from one colour to another. For the colour formation by subsequent reaction, many possibilities are known from which a selection can be made, depending upon the circumstances. For example, there are here mentioned those reactions in which the reduced electron acceptor becomes itself a part of a coloured compound, such as oxidative coupling reactions. However, colour-forming reactions can also be those in which the reduced electron acceptor, due to its reducing action on another substance, leads to a colour change thereof.

By "oxidation stage" is understood a numerical value which characterises the oxidation state of a particular atom in a compound, which can be a neutral molecule or a charged complex. The determination of oxidation stages is well known. Instructions for the determination of this numerical value are to be found in basic chemical text-books, for example "Anorganische Chemie", Hofmann & Rüdorff, pub Verlag F. Vieweg & Sohn, Braunschweig, 20th edition, 1969, page 216–219; "Lehrbuch der anorganischen Chemie", Hollemann-Wiberg, pub. Verlag Walter de Gruyter & Co., Berlin, 71st–80th edition, 1971, page 197–199, and "Anorganikum", ed. L. Kolditz, pub. VEB Deutscher Verlag der Wissenschaften, Berlin, 4th edition, 1972, page 446.

Electron acceptors preferred according to the present invention are N-oxides, nitroso compounds, hydroxylamines and oximes, N-oxides, nitroso compounds and oximes being especially preferred.

In particular, those N-oxides are advantageously used in which the nitrogen atom of the N-oxide carrying the oxygen atom is part of an aromatic ring system. Examples therefor include resazurin or resazurin derivatives as are described, for example, in European Patent Specification No. 0,156,347. The nitrogen atom of the N-oxide therein has the oxidation number $-1$.

Resazurin and resazurin derivatives are, as electron acceptors, reduced in the case of enzymatic oxidation to resorufins and resorufin derivatives, respectively, a distinct colour change being involved therewith. Thus, for example, resazuring has a blue colour and resorufin a red colour.

Furthermore, as advantageously usable aromatic N-oxides, there can be mentioned those of benzfuroxane and benzfuroxane derivatives, the carbon aromatic structure of which can be substituted by low molecular ring substituents. In this connection, low molecular ring substituents can be those with a molecular weight of up to about 400 Dalton.

Especially preferred benzfuroxanes have, for example, the general formula:

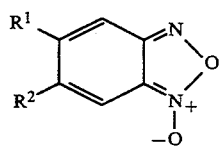

(I)

wherein $R^1$ and $R^2$ are the same or different and are hydrogen atoms or lower alkyl, lower alkoxy, lower alkylcarbonyl or formyl radicals.

In these compounds, the nitrogen atom of the N-oxide has the oxidation stage $+1$.

Lower alkyl and lower alkoxy are radicals containing up to 5 carbon atoms, methyl and methoxy radicals being especially preferred. Lower alkylcarbonyl are to be understood to be those radicals which contain up to 5 carbon atoms in the alkyl moiety, acetyl being especially preferred.

In the case of use of the above-mentioned benzfuroxanes of general formula (I) as electron acceptors in enzymatic oxidations, the colourless compounds are reduced to coloured compounds. Essentially, there takes place the formation of orange-coloured compounds.

For the process according to the present invention, the above-mentioned aromatic N-oxides can be used as direct colour indicators for the enzymatic oxidation of an analyte. For this purpose, the oxidising enzyme, together with the aromatic N-oxide, is brought into contact with the sample to be investigated. If the sample contains an analyte which can be oxidised by the enzyme, the N-oxide serves as electron acceptor which, by reduction, changes its colour and thus indicates the presence of the analyte in the sample. From the intensity of the newly formed colour, conclusions can be made regarding the concentration of the analyte in the sample.

Appropriate nitroso compounds which can be used for the process according to the present invention for the colorimetric determination of an analyte are preferably those which contain the nitroso radical bound to an aromatic group.

Especially preferred are carbon aromatic nitroso compounds, such as nitrosobenzene and nitrosobenzene derivatives. Nitrosobenzene derivatives which are quite outstandingly appropriate for the process according to the present invention are all those which are converted by reduction into those compounds which can serve for the colour formation in the sense of the previously given explanation.

Nitrosobenzene and nitrosobenzene derivatives are, as a rule, weakly coloured, yellow, green or brown coloured substances which, in the reduced state, are not coloured. In order to be able colorimetrically to indicate an analyte, these must, therefore, lead to a colour formation in a subsequent reaction. This can, for example, be achieved by reacting the reduced nitroso compound with another substance in such a manner that a coloured substance is obtained which contains the reduced nitroso compound as a partial structure thereof.

Oxidative coupling reactions are one possibility for this type of colour formation. Therefore, those nitroso compounds are especially preferred for the process according to the present invention which act not only as electron acceptors for oxidising enzymes but which can also be used in the reduced state for oxidative coupling reactions.

Quite especially preferred are nitrosobenzene derivatives of the general formula:

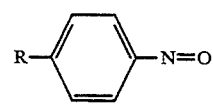

(II)

wherein R is a hydroxyl or amino group, the amino group being optionally substituted one or more times by lower alkyl radicals and the lower alkyl radicals can, in turn, be substituted by a hydroxyl group, an amino group mono- or polysubstituted by lower alkyl radicals, $PO_3H_2$, $SO_3H$ or COOH.

Outstandingly suitable are especially those nitrosobenzene derivatives of general formula (II) which have a low volatility.

In the above definition, a lower alkyl radical is one containing up to 5 carbon atoms, methyl and ethyl radicals being especially preferred.

The acid residues $PO_3H_2$, $SO_3H$ and $CO_2H$ can be present as such or in salt form as ammonium, alkali metal or alkaline earth metal salts. Ammonium salts are those which contain the unsubstituted ammonium cation $NH_4^+$ or those which contain ammonium cations substituted one or more times by lower alkyl, aryl and/or lower alkylaryl radicals. Lower alkyl means, in each case, an alkyl radical containing up to 5 carbon atoms and an aryl radical is an aromatic ring system containing 6 to 10 carbon atoms. Methyl and ethyl are preferred as lower alkyl, the preferred aryl radical is phenyl and benzyl is a preferred lower alkylaryl radical.

As electron acceptors for the process according to the present invention, p-hydroxynitrosobenzene, p-dimethylaminonitrosobenzene, p-diethylaminonitrosobenzene and p-dihydroxyethylaminonitrosobenzene are quite outstandingly preferred.

As stated above, for the process according to the present invention, nitrosobenzene or nitrosobenzene derivatives, in which nitrogen is present in the oxidation stage +1, are preferably brought into contact with the sample to be investigated and an oxidising enzyme. In the case of the presence of an analyte in the sample which is accepted as enzyme substrate, nitrosobenzene or a nitrosobenzene derivative functions as electron acceptor and is thereby reduced to the corresponding amine. As a rule, this reduction of the nitroso compounds does not suffice alone for a colorimetric determination of the analyte since either only colour decreases occur or colour changes are only weakly observable. However, the reduced electron acceptor can serve as starting material for an oxidative coupling reaction, in which case, depending upon the choice of the coupling partner, the most varied colours can be obtained.

Oxidative coupling reactions are well known and described, for example, in European Patent Specification No. 0,175,250 and in H. Hünig et al., Angewandte Chemie, 70, 215–222/1958. In general, oxidative couplings are frequently used for the production of dyestuffs. In this connection, they can be regarded as being a reaction between an electron-rich aromatic compound and an oxidisable coupling component which takes place in the presence of oxidation agents, for example sodium or potassium ferricyanide, copper salts, mercury salts, ferric chloride, lead dioxide, hydrogen peroxide, lead tetraacetate, sodium or potassium salts of per sulphuric acid, peracetic acid, periodic acid or chloramine T. According to Federal Republic of Germany Patent Specification No. 33 31 588, oxidases can also be used as oxidation agents. The above described nitrosobenzenes represent in their reduced state, after they have acted as electron acceptors in enzymatic oxidations, compounds which, as oxidisable coupling components, are available for oxidative coupling reactions. For this purpose, the amines resulting due to the reduction can be oxidised by oxidation agents, as have been mentioned above by way of example, in order to form a coloured material with electron-rich coupling components simultaneously present in the reaction mixture.

A plurality of electron-rich coupling components are available. These coupling components can be chosen depending upon the desired colour of the coupling product. Examples thereof include aromatic amines, phenols and methylene-active compounds. Especially preferred compounds can be chosen from the group consisting of the anilines, for example N-methylanthranilic acid, and the anilinophosphonic acids mentioned in European Patent Specification No. 0,175,250.

A further possibility for the determination of the reduced electron acceptor by colour formation consists, in the case of the nitroso compounds, in oxidising the reduced nitroso compounds by other substances which, on the basis of this transition from the oxidised into the reduced form, form a colour. Here, too, by colour formation is to be understood not only the transition from one colour to the other but also from the colourless into the coloured state. Examples of such colour forming reactions include, for example, the oxidation of the reduced electron acceptor by means of metal salts which are thereby reduced to coloured metal salts with the metal in a lower oxidation stage or possibly completely reduced to the neutral metal. Cupric salts can, for example, be converted into red cuprous salts and silver salts into metallic silver. The reduction of phosphomolybdate to molybdenum blue is also possible.

Instead of aromatic nitroso compounds, for the process according to the present invention, there can also be used aromatic oximes as electron acceptors for enzymatic oxidations. Nitroso compounds can be in a tautomeric equilibrium with oximes. This is especially the case when, for this purpose, a hydrogen atom is available in the α-position to the nitroso group:

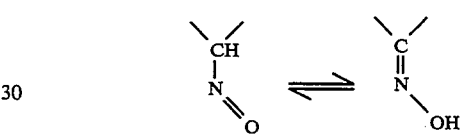

or when a corresponding delocalisation of the electrons and protons is possible.

We have found that oximes which, with nitroso compounds which function as electron acceptors in enzymatic oxidation reactions, can stand in a tautomeric nitroso/oxime equilibrium, can also be used in the process according to the present invention. This applies especially to oximes of the general formula:

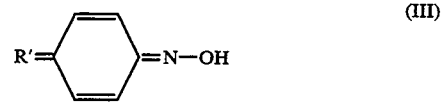

(III)

in which R' is an oxygen atom, a further oxime group or a positively charged amino group, the amino group optionally being substituted once or twice by lower alkyl radicals and the lower alkyl radicals can, in turn, be substituted by a hydroxyl group, an amino group substituted one or more times by lower alkyl $PO_3H_2$, COOH or $SO_3H$.

In the above definition, lower alkyl means an alkyl radical containing up to 5 carbon atoms, methyl and ethyl radicals being especially preferred.

The acid residues $PO_3H_2$, $SO_3H$ and COOH can be present as such or in salt form as ammonium, alkali metal or alkaline earth metal salts.

Ammonium salts are those which contain the unsubstituted ammonium cation $NH_4^+$ or those which contain ammonium cations substituted one or more times by lower alkyl, aryl and/or lower alkylaryl radicals. Lower alkyl means, in each case, an alkyl radical containing up to 5 carbon atoms and the aryl radical is an aromatic ring system containing 6 to 10 carbon atoms. Methyl and ethyl are preferred as lower alkyl radicals, the preferred aryl radical is phenyl and benzyl is a preferred lower alkylaryl radical. In such oximes, the nitrogen has the oxidation stage −1.

In the same way as the nitrosobenzenes, the oximes of general formula (III) are also colourless or coloured substances which, in the reduced state, are not coloured. As described above for nitrosobenzenes as electron acceptors in the process according to the present invention, aromatic oximes, after functioning as electron acceptors, can also be brought to colour formation. Not only nitroso compounds but also oximes give amines in the case of exhaustive reduction. For oximes as electron acceptors, in the process according to the present invention, fundamentally the same subsequent reactions can be used for the colour formation as for the nitroso compounds.

Hydroxylamines which can be used as electron acceptors for the process according to the present invention are preferably also aromatic compounds. Especially phenylhydroxylamine derivatives substituted in the phenyl ring can be used as electron acceptors for the process according to the present invention. In these compounds, the nitrogen atom has the oxidation number −1.

Quite especially preferred phenylhydroxylamines are those of the general formula:

(IV)

wherein R″ has the same meaning as R in general formula (II).

Hydroxylamines are also converted by reduction into the corresponding amines which are not essentially coloured. Therefore, as described for the nitroso compounds and oximes, following the oxidation of the analyte and the reduction of the electron acceptor involved therewith according to the process of the present invention, subsequent reactions must take place which, starting from the reduced electron acceptor, give rise to a colour formation. Fundamentally, there applies therefor the same as already stated for the use of nitroso compounds or oximes as electron acceptors in the process according to the present invention. Starting compounds for all these subsequent reactions are the electron acceptors of the enzymatic oxidation reduced to the stage of the amine.

Surprisingly, we have found that compounds with nitrogen in an oxidation stage between +1 and −1 and preferably those with an oxidation stage of +1 or −1, especially compounds selected from the group comprising N-oxides, nitroso compounds, oximes and hydroxylamines, and quite especially compounds selected from the group comprising N-oxides, nitroso compounds and oximes, as are described above, can serve as colour-forming electron acceptors for many enzymatic oxidations which are catalysed by oxidoreductases. Preferably, they can be used where, for the electron transfer from the analyte to be oxidised to the colour-forming electron acceptor, no reduction catalysts, such as diaphorase or N-methylphenazinium methosulphate, are desired. Surprisingly, we have found that these substances are advantageous when oxidases or non-NAD(P)-dependent dehydrogenases are used as oxidising enzymes. If such enzymes are used for the oxidation of an analyte, the electron transfer can take place directly, i.e. without the cooperation of a reduction catalyst, from the analyte/enzyme system to the above-mentioned colour-forming electron acceptors. As analyte/enzyme system, in this connection, is to be understood the combination necessary for the oxidation reaction of analyte and oxidising enzyme, as well as possibly together with co-enzymes and/or co-factors, such as for example metal salts, naturally necessary for the oxidation and working together with the enzyme.

For the process according to the present invention, (flavin-dependent) oxidases are especially preferred. Examples include L- and D-amino acid oxidases, cholesterol oxidase, glucose oxidase, glycerol-3-phosphate oxidase, lactate oxidase and pyruvate oxidase. Oxidases which, according to the present invention, are quite especially preferred include glucose oxidase, glycerol-3-phosphate oxidase, lactate oxidase and pyruvate oxidase.

Of the non-NAD(P)-dependent dehydrogenases, pyrroloquinoline-quinone (PQQ)-dependent dehydrogenases can be especially advantageously used for the process according to the present invention. Especially glucose dehydrogenase is very appropriate for the colorimetric determination of glucose in the presence of compounds with nitrogen in an oxidation stage between +1 and −1 as colour-forming electron acceptors. In the same way, non-NAD(P)-dependent alcohol dehydrogenase can be used for the determination of alcohols, such as ethanol.

The process according to the present invention is carried out in such a manner that the sample to be investigated is contacted with an appropriate oxidoreductase and one or more of the above-described colour-forming electron acceptors. If the sample contains an analyte which is oxidised by the oxidoreductase, the colour-forming electron acceptor is reduced. If the reduced electron acceptor displays a colour other than that of the original electron acceptor in its oxidised form or if the electron acceptor, due to the enzymatic oxidation procedure, passes over from a colourless state into a coloured state, the intensity of the colour formed can be correlated directly visually, possibly by comparative colours, or photometrically with the concentration of the analyte in the sample. If the colour of the reduced electron acceptor is substantially the same as that of the electron acceptor originally used or if a colour lightening or complete decolorisation takes place, then a following reaction is attached to the enzymatic oxidation reaction which leads to a colour from the intensity of which the concentration of the analyte in the sample can also be determined visually or photometrically.

The process can be carried out in a so-called wet test, for example in a cuvette, or as a so-called dry test on an appropriate reagent carrier, the necessary test reagents thereby being present in a solid carrier, which is preferably an absorbent or swellable material. Such test carriers are known, for example, from European Patent Specifications Nos. 0,016,387, 0,262,445 and 0,256,806 and from Federal Republic of Germany Patent Specification No.32 47 608.

Agents for the colorimetric determination of an analyte for carrying out the process according to the present invention, such as are described in the claims, are also the subject of the present invention. Such an agent contains, besides the oxidoreductase necessary for the enzymatic oxidation of the analyte to be determined, at least one colour-forming electron acceptor which takes over the electrons liberated in the case of the oxidation directly from the analyte/enzyme system. As oxidising enzymes and colour-forming electron acceptors, there are used the materials described above for the process according to the present invention.

For the maintenance of a pH value appropriate for carrying out the process, which depends especially upon the enzymes to be used, the agent according to the present invention contains a buffer system. Furthermore, it can contain further appropriate additive materials usually employed for such agents, for example wetting agents, stabilisers and the like. If the oxidation of the electron acceptor does not lead to a measurable colour change, for the colorimetric determination of an analyte, the agent according to the present invention naturally also includes the reagents necessary for a subsequent reaction.

The agent according to the present invention can be present in the form of a solution or can be applied to an absorbent or swellable carrier. In the form of a solution, the agent preferably contains all the reagents needed for the process according to the present invention. As solvents, there can be used water, water-soluble organic solvents, for example methanol, ethanol, acetone or dimethylformamide, or mixtures of water with such organic solvents. For reasons of storage stability, it can be advantageous to divide the reagents needed for the test into two or more solutions which are first mixed in the case of the actual investigation. The latter can especially apply when, after oxidation of the analyte, the reduced electron acceptor is further reacted in a subsequent reaction, for example an oxidative coupling reaction. Typical concentrations for the electron acceptors used in the agent according to the present invention are from 0.01 to 100 mMol/liter and preferably from 0.1 to 25 mMol/liter. Reagents for subsequent reactions are used at least in stoichiometric relationship to the electron acceptors, preferably in an excess and especially in a 2 to 10 fold excess.

The agent according to the present invention can also be present in the form of a test strip. Such test strips are known in many embodiments, for example from European Patent Specifications Nos. 0,016,387, 0,262,445 and 0,256,806 and from Federal Republic of Germany Patent Specification No. 32 47 608. It is common to all that the reagents needed for carrying out the determination process are present on solid carrier layers. As carrier layers, there are especially preferred absorbent and/or swellable materials which are wetted by the sample liquid to be investigated. Examples therefor include gelatine, cellulose and synthetic fibre fleece. The reagents are present in solid form in or on these carrier materials.

In the case of the application of the sample liquid to the test strips or dipping of the test strips into the sample liquid, a liquid medium forms in the strips within which the detection reaction takes place. The colour formation caused by the reaction can be evaluated visually or photometrically, for example reflection photometrically.

A special subject of the present invention concerns the use of a substance selected from the group of compounds with nitrogen in an oxidation stage between $+1$ and $-1$ as direct electron acceptor of an analyte/oxidoreductase system. As analyte/oxidoreductase system, in this connection there is to be understood the combination necessary for an enzymatic oxidation reaction of analyte and oxidising enzyme, as well as possibly together with co-enzymes, such as flavine or PQQ and/or cofactors, for example metal salts, naturally necessary for the oxidation working together with the enzyme. We have found that substances selected from the group consisting of nitroso compounds, N-oxides, hydroxylamines and oximes can be used quite generally as colour-forming electron acceptors in the case of the oxidation of an analyte by means of an oxidoreductase.

The present invention offers the advantage that no reduction catalysts, such as diaphorase or N-methylphenazinium methosulphate, are necessary for the reduction of a colour-forming electron acceptor. The reduction thereof can now take place directly by the analyte/enzyme system. Possibly disturbing side reactions can thus be avoided.

Especially in the case of the use of oxidases for the enzymatic oxidation of analytes, by means of the use of the compounds according to the present invention, the formation of hydrogen peroxide as precursor of a colorimetric determination process is avoided. This removes or reduces the disturbing influence of reducing-acting compounds.

Finally, the compounds employed according to the present invention offer a true alternative where the admission of atmospheric oxygen is limited or undesired. Oxygen can, as electron acceptor, be replaced by these compounds in the case of enzymatic oxidations. This offers quite special advantages in the case of agents according to the present invention in the form of test strips. Whereas these hitherto, especially in the case of high analyte concentrations, had to be so constructed that, in the case of enzymatic oxidations by means of oxidase, atmospheric oxygen had admission to the reagent mixture applied to the test strips, test strips can now be constructed which operate especially quickly and dependably. Thus, whereas previously in the case of test strips, after application to the test strips the sample had often to be wiped off again after a certain time in order that oxygen could diffuse at all into the test strips, this measure is not necessary when using the electron acceptors according to the present invention. Since the time-dependent diffusion of oxygen into the test strips is avoided, in the case of kinetic measurements, there are obtained reaction velocities dependent upon the analyte concentration and, in the case of end point measurements, in the end point are obtained reaction velocities independent of the analyte concentration which permit a determination process which is quicker, more dependable and simpler than was previously possible.

The following Examples are given for the purpose of illustrating the present invention:

EXAMPLE 1

Reduction of N-oxides by oxidases or non-NAD(P)-dependent dehydrogenases and their substrates A)
40 g. polyvinyl propionate (e.g. Propiofan 70 D, BASF AG, Ludwigshafen, Federal Republic of Germany)
45 g. sodium alginate (e.g. Algipon of Kelco, division of Merck & Co., Clark, N.J., USA)
2.5 g. protein hydrolysate (e.g. crotein C, Croda GmbH, Nettetal, Federal Republic of Germany)
10 ml. tris buffer, 0.1M, pH 7.5
750 IU glucose oxidase (EC 1.1.3.4) and
1 ml. resazurin 0.1M in water were stirred to give a homogeneous mass, raked out in thickness of 140 μm. on polycarbonate film, one side of which was matt (e.g. Pokalon, Lonza, Rheinfelden, Federal Republic of Germany) (rake clearance 200 μm.) and dried at 50° C. for 30 minutes.

Upon applying a glucose-containing solution (40 mg./dl.) to such a film, the reagent layer changes colour within 1 minute from blue to red. The presence of 20 mg./ml. uric acid and 20 mg./ml. glutathione does not lead to any disturbance of the colour reaction. When applying solutions which do not contain glucose, the reagent layer retains the colour which it had before the sample application, i.e. it remains blue.

Instead of with glucose and glucose oxidase, the same colour result was also achieved with pyruvate and pyruvate oxidase (EC 1.2.3.3), lactate and lactate oxidase (EC 1.1.3.2) and glycerol-3-phosphate and glycerol-3-phosphate oxidase (EC 1.1.3.21).

B) If, in the case of the production of the above-described film, instead of resazurin, the following benzfuroxanes were used:

a) $R^1 = R^2 = H$
b) $R^1 = H$; $R^2 = COCH_3$ (preparation according to N. R. Ayyangov, Synthesis, 1987, 616)
c) $R^1 = H$; $R^2 = CHO$ (preparation according to M. L. Edwards, J. Het. Chemistry, 13, 653/1976)
d) $R^1 = R^2 = CH_3$ (preparation according to J. A. Usta et al., J. Het. Chemistry, 18, 655/1981)

in a concentration of 250 mg. per film batch, then in each case the colour changes in the presence of glucose in the sample investigated from colourless to orange, the colour intensity increasing with increasing glucose concentration.

The presence of 20 mg./ml. uric acid did not lead to a disturbance of the colour reaction.

The substrate/enzyme pairs pyruvate/pyruvate oxidase (EC 1.2.3.3), lactate/lactate oxidase (EC 1.1.3.2) and glycerol-3-phosphate/glycerol-3-phosphate oxidase (EC 1.1.3.21) could also be detected with the above-mentioned benzfuroxanes.

EXAMPLE 2

Reduction of nitroso compounds by glucose oxidase and glucose

A)
2000 μl. 0.1M citric acid/sodium hydroxide buffer, pH 6.0
200 μl. p-nitroso-N,N-dimethylaniline, 0.1M in ethanol
100 μl. glucose oxidase (EC 1.1.3.4) (2500 IU/ml.) or glucose dehydrogenase (EC 1.1.99.10)
200 μl. sample with known glucose content
a) 5 mM
b) 10 mM
c) 15 mM
d) 20 mM
e) 50 mM in water were mixed and incubated at 25° C. for 2 minutes. There were then added thereto 250 μl. N-methylanthranilic acid, 0.1M in ethanol 125 μl. potassium ferrocyanide, 0.2M in water and 125 μl. potassium ferricyanide, 0.2M in water. After a further minute, 25 fold dilution was carried out and the absorption of the reaction mixture, which became green coloured in the case of the presence of glucose, measured at 710 nm against a blank (above reaction mixture without glucose). The results obtained gave a line. The extinction coefficient of $\epsilon_{710} = 24000$ $M^{-1}$ $cm^{-1}$ can be used for the determination of unknown glucose concentrations in solutions.

B) If, in the case of the above test, in A) p-nitrosodimethylaniline was replaced by
a) p-nitrosophenol
b) p-nitroso-N,N-diethylaniline
c) p-nitroso-N,N-diethanolaniline (preparation according to D'Amico et al., J.A.C.S., 81, 5957/1959)

then, in the case of the presence of glucose, due to the coupling with N-methylanthranilic acid, a colour change of
a) brown to blue
b) yellow to green
c) yellow to green
was observed.

C) If, in the case of the above test, in A) N-methylanthranilic acid was replaced by
a) N-methyl-N-methylenephosphonic acid aniline
b) 1-hydroxynaphthalene-2-carboxylic acid
c) aniline-2-sulphonic acid then, in the case of the presence of glucose, due to the coupling with p-nitroso-N,N-dimethylaniline, a colour with
a) $\lambda_{max} = 735$ nm
b) $\lambda_{max} = 590$ nm
c) $\lambda_{max} = 640$ nm
was observed.

In the case of the use of p-nitroso-N,N-dimethylaniline and N-methyl-N-methylenephosphonic acid aniline, there was found the dependence shown in FIG. 1 of the accompanying drawings of the change of the light absorption at 735 nm upon the glucose concentration. For this purpose, the extinction was measured after (1+24) dilution in citrate buffer (pH 6) and plotted against the glucose concentration in the test batch.

EXAMPLE 3

Detection of glucose by formation of metallic silver

The batch of citrate buffer, p-nitroso-N,N-dimethylaniline, glucose oxidase and sample was incubated for 2 minutes at 25° C. as in Example 2 A and mixed with 250 μl. 100 mM silver nitrate solution in water, as well as with 250 μl. gold sol in water.

(The preparation of gold sol took place according to the following procedure: To 100 ml. boiling distilled water were successively added 0.4 mg. chloroauric acid ($HAuCl_4$) in 0.4 ml. of water; 0.2 ml. 0.1M sodium thiocyanate in water and 0.5 ml. 0.1M potassium carbonate in water. After 10 minutes, it was left to cool).

Figure 2:
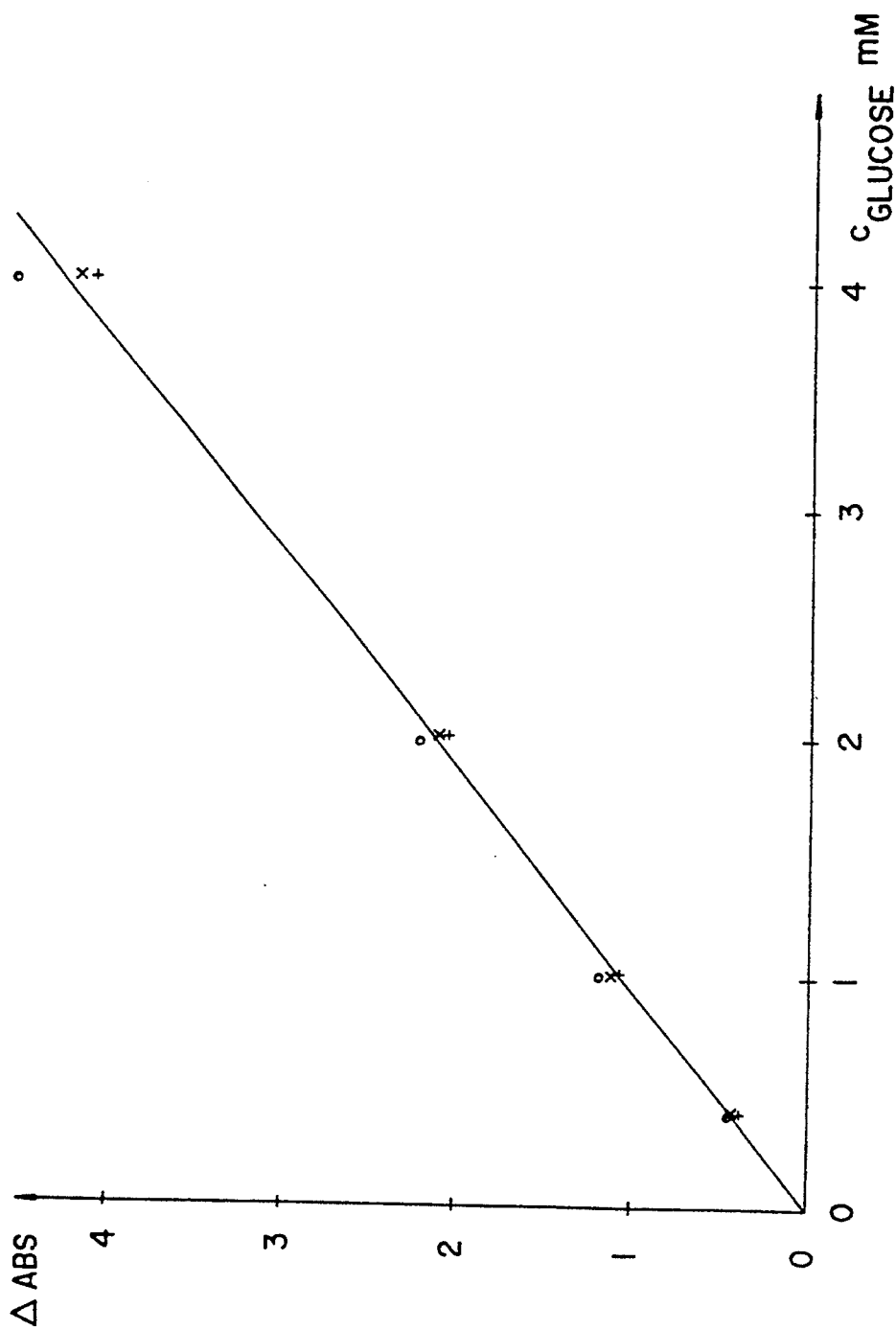
FIG. 2 is a plot of change of light absorption at 700, 850 and 1300 nm versus glucose concentration for a test sample described in Example 3.

With the results obtained without intermediate dilution at 700, 850 and 1300 nm, there was obtained the curve shown in FIG. 2 of the accompanying drawings. It can serve as a calibration curve for the determination of the unknown glucose content in solutions.

EXAMPLE 4

Detection of glucose by molybdenum blue formation

To a solution of 200 mg. 2,18-phosphomolybdic acid (preparation possible, for example, according to G.

Figure 3:
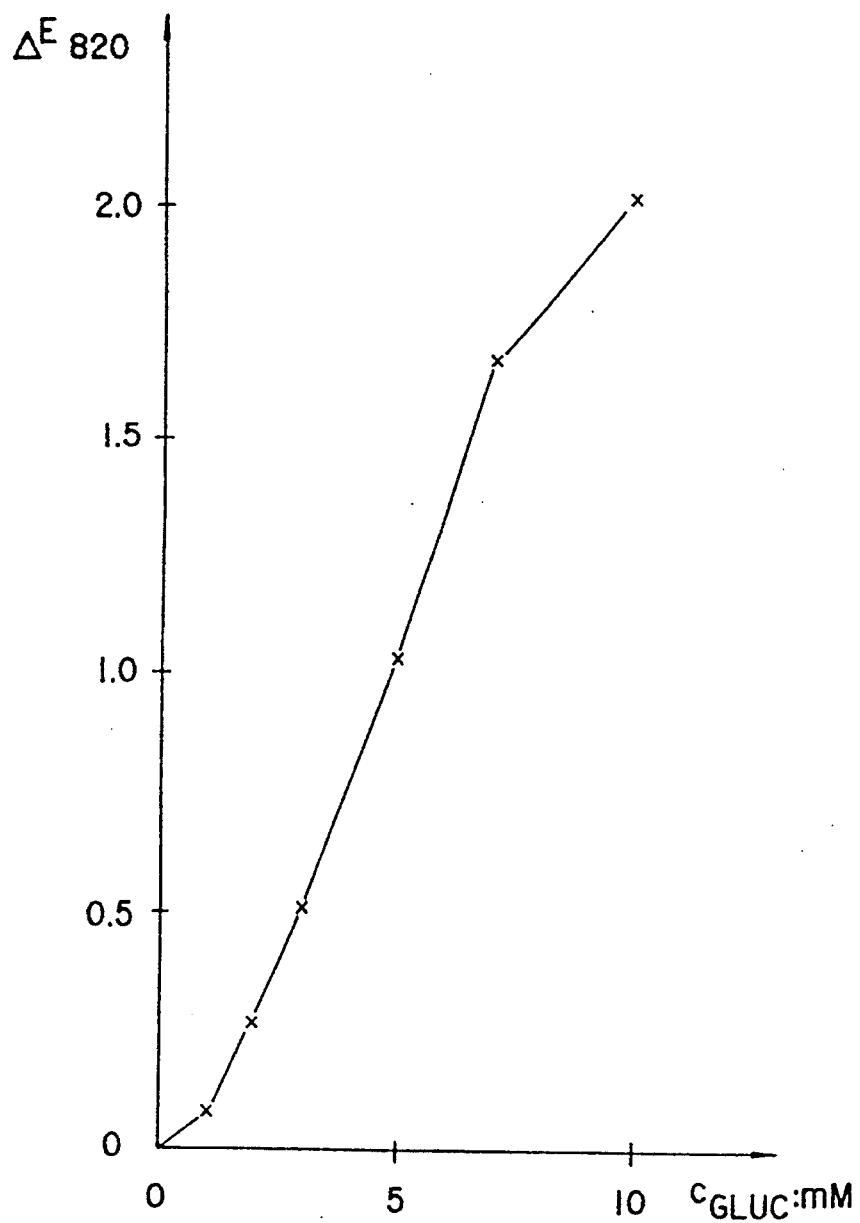
FIG. 3 is a plot of change of light absorption at 820 nm versus glucose concentration for a test sample described in Example 4.

Brauer, "Handbuch der praparativen Anorganischen Chemie", pub. Enke-Verlag Stuttgart, p 1278, 1954 or A. Rosenheim and A. Traube, Z. Anorg. Chemie, 65., 99/1910) in 920 -x μl. 0.1M citric acid/sodium hydroxide buffer (pH 5.5) were added 40 μl 0.1M p-nitroso-N,N-dimethylaniline (in ethanol), as well as 40 μl. glucose oxidase (6250 IU/ml. water ). 1 Minute after the addition of x μl. (x=0, 1, 2, 3, 5, 7, 10) of a glucose-containing sample of known glucose content (1M), the solution was diluted to 50 ml. and the absorption change ($\Delta E$) measured at 820 nm. As result, there was obtained the curve shown in FIG. 3 of the accompanying drawings. It can serve as a curve for the determination of the unknown glucose content of solutions, C representing the concentration in the sample before the dilution carried out for the measurement.

EXAMPLE 5

Kinetic determination of glucose by means of non-NAD(P)-dependent glucose dehydrogenase The following solutions were prepared:

test buffer: 0.1M tris/hydrochloric acid, pH 7.5, containing 1% bovine serum albumin electron acceptor: 0.1M p-nitroso-N,N-dimethylaniline in ethanol indicator: 2,18-phosphomolybdic acid, 100 mg./ml.water enzyme: glucose dehydrogenase (EC 1.1.99.17), 50 IU/ml. test buffer glucose solution:
 a) 36 mg. glucose/dl. human plasma
 b) 72 mg. glucose/dl. human plasma
 c) 144 mg. glucose/dl. human plasma
 d) 360 mg. glucose/dl. human plasma
 e) 720 mg. glucose/dl. human plasma
 f) 1440 mg. glucose/dl. human plasma
 g) 3600 mg. glucose/dl. human plasma In a 1 cm. cuvette were placed
1740 μl. buffer
250 μl. electron acceptor
250 μl. indicator and
10 μl. glucose dehydrogenase,
the mixture thermostated at 25° C. and then 250 μl. glucose solution added thereto. With the addition of the glucose as the starting point, the absorption change per minute ($\Delta E$/min.) was recorded at 820 nm, the following values being obtained:

| glucose concentration (end concentration in the test batch) | $\Delta$ E/min. |
|---|---|
| 3.6 mg./dl. | 0.20 |
| 7.2 mg./dl. | 0.38 |
| 14.4 mg./dl. | 0.57 |
| 36 mg./dl. | 1.00 |
| 72 mg./dl. | 1.60 |
| 144 mg./dl. | 2.24 |
| 360 mg./dl. | 3.13 |

EXAMPLE 6

Test strips for glucose detection by molybdenum blue formation 1 g. sodium alginate (e.g. Algipon of Kelco, division of Merck & Co., Clark, N.J., USA)

45 g. polyvinyl propionate (e.g. Propiophan 70D of BASF, Ludwigshafen, Federal Republic of Germany)

0.75 g. sodium nonyl sulphate 10.15 g. potassium dihydrogen phosphate and 58.5 g. distilled water 4 g. Aerosil COK 84 (Degussa, Hanau, Germany/FRG) were stirred to give a homogeneous mass and adjusted to pH 5.5 with 10N aqueous sodium hydroxide solution.

Subsequently, there were then added thereto 65 mg. glucose oxidase (250 IU/mg.)

260 mg. p-nitroso-N,N-dimethylaniline 1.3 g. 2,18-phosphomolybdic acid.

The mass was raked out in 320 μm. layer thickness on a 1 mm. thick polystyrene foil and dried at 60° C. for 1 hour. Upon applying a drop of a glucose-containing solution, a distinct green coloration occurred within one minute. The intensity of the coloration increased with increasing glucose concentration and could be evaluated visually on the basis of a comparison scale or reflection photometrically.

Instead of the electron acceptor p-nitroso-N,N-dimethylaniline, there could also be used p-benzoquinone dioxime or p-nitroso-N,N-diethanolaniline.

In the case of storage in the dark at ambient temperature, the coloration was stable for several weeks.

If, in the above Example, p-nitroso-N,N-dimethylaniline is replaced by peroxidase (100 mg.; 200 IU/mg.) and phosphomolybdic acid by 3,3',5,5'-tetramethylbenzidine (300 mg.), then an oxygen-dependent glucose test is obtained, as is known in principle from the prior art. In contradistinction to the above Example, however, the sample solution, after application to the test strip, must be wiped off in order that oxygen can diffuse in and for coloration to take place at all. In addition to this disadvantage, the end coloration with comparatively high glucose concentrations is achieved ever more slowly and the colour produced is less storage stable. The advantages of the replacement of oxygen by electron acceptors according to the present invention are thus:

no wiping off of the sample after application to the test strip is necessary;

quicker reaction;

in the case of kinetic measurement, the speed of reaction is dependent upon the analyte concentration; in the case of end point measurement, at the end point the speed of reaction is independent of the analyte concentration;

more stable coloured material.

EXAMPLE 7

Detection of glucose with non-NAD(P)-dependent glucose dehydrogenase and resazurin To 2050 μl. of test buffer (0.2M citrate, 1% by weight albumin, pH 7.0) and 100 μl. electron acceptor solution (10 mM resazurin in water) were added in a cuvette 250 μl. of sample solution ($C_{glucose}$=0 to 0.5 mM) and 100 μl. of enzyme solution (glucose dehydrogenase (EC 1.1.99.17); 200 U/ml. in test buffer). After 2 minutes, the absorption was measured at 530 nm against an identically treated blank with 100 μl. of test buffer instead of enzyme solution. The following results were obtained:

| glucose concentration in | | absorption change |
| --- | --- | --- |
| (mM) cuvette | (mM) sample | Δ E₅₃₀ |
| 0 | 0 | 0 |
| 0.002 | 0.02 | 0.009 |
| 0.004 | 0.04 | 0.018 |
| 0.008 | 0.08 | 0.035 |
| 0.012 | 0.12 | 0.051 |
| 0.016 | 0.16 | 0.068 |
| 0.020 | 0.20 | 0.087 |
| 0.030 | 0.30 | 0.130 |
| 0.040 | 0.40 | 0.174 |
| 0.050 | 0.50 | 0.217 |

Up to a sample concentration of 0.5 mM, the test is linear. In this range, the concentration in the cuvette can be calculated from the extinction coefficient $\epsilon_{530}=4350 M^{-1}\,cm^{-1}$. In the case of higher sample concentrations, intermediate dilution can be carried out or a smaller sample volume used. Lower sample concentrations can be sensitively determined on the basis of the fluorescence of the product resorufin.

In an analogous way, the test can be carried out with benzfuroxane and the benzfuroxane derivatives mentioned in Example 1 B), as well as with the nitroso compounds according to Example 2.

Ethanol can be detected in the same way with non-NAD(P)-dependent alcohol dehydrogenase (EC 1.1.99.8).

EXAMPLE 8

Determination of lactate with lactate oxidase and nitroso compounds as electron acceptor In a cuvette, 2240 μl. of test buffer (0.2M citric acid/-sodium hydroxide, pH 6.35), 5 μl. of electron acceptor (0.1M N,N-dimethyl-p-nitrosoaniline in ethanol) and 250 μl. of sample with known lactate concentration were mixed and thermostated to 25° C. The test was started with 5 μl. of enzyme solution (lactate oxidase from *Pediococcus sp.*), 200 U/ml. of test buffer) and the change of extinction ΔE/min. recorded at 390 nm. The following results were obtained:

| $C_{lactate}$: mM | Δ E/min. |
| --- | --- |
| 0 | 0 |
| 0.1 | 0.093 |
| 0.2 | 0.182 |
| 0.3 | 0.250 |
| 0.5 | 0.343 |
| 1.0 | 0.443 |
| 3.0 | 0.508 |

$C_{lactate}$ is thereby the lactate concentration which is present in the cuvette in the case of carrying out the measurement.

The test could be accelerated or slowed down by changes of the electron acceptor concentration, enzyme concentration, observation wavelength and temperature. As electron acceptor, there can also be used N,N-diethyl-p-nitrosoaniline, N,N-bis-(2-hydroxyethyl)-p-nitrosoaniline, benzfuroxane and resazurin.

I claim:

1. A composition for use in the colorimetric determination of an analyte comprising
  a) an oxidoreductase enzyme dependent from the cofactors flavine or PQQ which is effective to oxidize the analyte;
  b) an aromatic nitroso compound or a tautomerically equivalent oxime compound which is effective to accept electrons from the enzyme/cofactor to cause a color change in the reaction mixture; and
  c) a coupling reagent for an oxidative coupling reaction.

2. The composition according to claim 1, wherein the aromatic nitroso compound is a nitroso benzene derivative of the formula

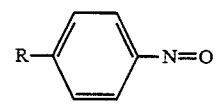
(II)

wherein R is hydroxyl or amino group, the amino group being optionally substituted by one or more lower alkyl radicals which can be substituted by a hydroxyl group, or by an amino group substituted by one or more lower alkyl radicals, PO₃H₂, SO₃H or COOH.

3. The composition according to claim 2, wherein R is a hydroxyl, dimethylamino, diethylamino or dihydroxylethylamino group.

4. The composition according to claim 1, wherein the oxime compound is an oxime of the formula III

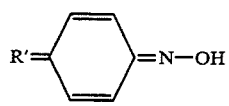
(III)

wherein R' is an oxygen atom, a further oxime group or a positively charged amino group, the amino group optionally being substituted by one or two lower alkyl radicals which can be substituted by a hydroxyl group or an amino group substituted by one or more lower alkyl radicals, PO₃H₂, COOH or SO₃H.

5. The composition according to any one of claims 1-4, wherein the oxidoreductase is a flavin-dependent oxidase selected from the group consisting of L- or D-amino acid oxidase, cholesterol oxidase, glucose oxidase, glycerol-3-phosphate oxidase, lactate oxidase and pyruvate oxidase.

6. The composition according to any one of claims 1-4; wherein the PQQ-dependent oxidoreductase is PQQ-dependent glucose dehydrogenase.

7. The composition according to any one of claims 1-4; wherein the PQQ-dependent oxidoreductase is a PQQ-dependent alcohol dehydrogenase.

8. A composition for use in the colorimetric determination of an analyte comprising
  a) an oxidoreductase enzyme dependent from the cofactors flavine or PQQ which will oxidize the analyte;
  b) an aromatic nitroso compound or a tautomerically equivalent oxime compound which will accept electrons from the enzyme/cofactor to cause a color change in the reaction mixture; and
  c) a substance which forms a color by transition from the oxidized form into the reduced form.

9. The composition according to claim 8, wherein the aromatic nitroso compound is a nitroso benzene derivative of the formula

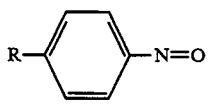

wherein R is hydroxyl or amino group, the amino group being optionally substituted by one or more lower alkyl radicals which can be substituted by a hydroxyl group, or by an amino group substituted by one or more lower alkyl radicals, $PO_3H_2$, $SO_3H$ or COOH.

10. The composition according to claim 9, wherein R is a hydroxyl, dimethylamino, diethylamino or dihydroxylethylamino group.

11. The composition according to claim 8, wherein the oxime compound is an oxime of the formula III

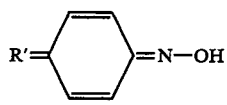

wherein R' is an oxygen atom, a further oxime group or a positively charged amino group, the amino group optionally being substituted by one or two lower alkyl radicals which can be substituted by a hydroxyl group or an amino group substituted by one or more lower alkyl radicals, $PO_3H_2$, COOH or $SO_3H$.

12. The composition according to any one of claims 8–11, wherein the oxidoreductase is a flavin-dependent oxidase selected from the group consisting of L- or D-amino acid oxidase, cholesterol oxidase, glucose oxidase, glycerol-3-phosphate oxidase, lactate oxidase and pyruvate oxidase.

13. The composition according to any one of claims 8–11, wherein the PQQ-dependent oxidoreductase is a PQQ-dependent glucose dehydrogenase.

14. The composition according to any one of claims 8–11, wherein the PQQ-dependent oxidoreductase is a PQQ-dependent alcohol dehydrogenase.

15. A composition for use in the colorimetric determination of an analyte comprising a) an oxidoreductase enzyme dependent from the cofactor PQQ which will oxidize the analyte;

b) an aromatic nitroso compound or a tautomerically equivalent oxime compound which will accept electrons from the enzyme/cofactor to cause a color change in the reaction mixture.

16. The composition according to claim 15, wherein the aromatic nitroso compound is a nitroso benzene derivative of the formula

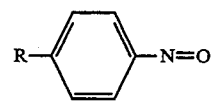

wherein R is hydroxyl or amino group, the amino group being optionally substituted by one or more lower alkyl radicals which can be substituted by a hydroxyl group, or by an amino group substituted by one of more lower alkyl radicals, $PO_3H_2$, $SO_3H$ or COOH.

17. The composition according to claim 16, wherein R is a hydroxyl, dimethylamino, diethylamino or dihydroxylethylamino group.

18. The composition according to claim 15, wherein the oxime compound is an oxime of the formula III

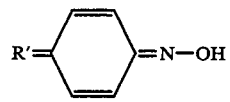

wherein R' is an oxygen atom, a further oxime group or a positively charged amino group, the amino group optionally being substituted by one or two lower alkyl radicals which can be substituted by a hydroxyl group or an amino group substituted by one or more lower alkyl radicals, $PO_3H_2$, COOH or $SO_3H$.

19. The composition according to any one of claims 15–18, wherein the PQQ-dependent oxidoreductase is a PQQ-dependent glucose dehydrogenase.

20. The composition according to any one of claims 15–18, wherein the PQQ-dependent oxidoreductase is a PQQ-dependent alcohol dehydrogenase.

* * * * *